(12) United States Patent
Haechler

(10) Patent No.: US 9,505,012 B2
(45) Date of Patent: *Nov. 29, 2016

(54) AUTOMATED SAMPLE WORKCELL AND METHOD OF OPERATION

(71) Applicant: Roche Diagnostics Operations, Inc., Indianapolis (IN)

(72) Inventor: Joerg Haechler, Oberwil b. Zug (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 454 days.

This patent is subject to a terminal disclaimer.

(21) Appl. No.: 14/087,342

(22) Filed: Nov. 22, 2013

(65) Prior Publication Data

US 2014/0080693 A1  Mar. 20, 2014

Related U.S. Application Data

(62) Division of application No. 13/077,468, filed on Mar. 31, 2011, now Pat. No. 8,617,041.

(30) Foreign Application Priority Data

Apr. 1, 2010  (EP) .................................. 10158946

(51) Int. Cl.
*B04B 13/00* (2006.01)
*G01N 35/00* (2006.01)
*B04B 11/04* (2006.01)

(52) U.S. Cl.
CPC ........... *B04B 13/00* (2013.01); *G01N 35/0092* (2013.01); *B04B 2011/046* (2013.01); *G01N 35/0095* (2013.01); *G01N 2035/0094* (2013.01); *Y10T 436/111666* (2015.01)

(58) Field of Classification Search
CPC ............ B04B 13/00; B04B 2011/046; G01N 35/0092; G01N 35/0095; G01N 2035/0094; Y10T 436/111666
See application file for complete search history.

(56) References Cited

U.S. PATENT DOCUMENTS 5,865,718 A  2/1999  Chan
6,060,022 A  5/2000  Pang et al.
(Continued)

FOREIGN PATENT DOCUMENTS

WO  89/06162 A1  7/1989
WO  2007/018897 A2  2/2007

*Primary Examiner* — Timothy Cleveland
(74) *Attorney, Agent, or Firm* — Barnes & Thornburg LLP

(57) ABSTRACT

Illustrative embodiments of automated sample workcells and methods of operation are disclosed. The methods may include receiving a first plurality of samples, each of the first plurality of samples being linked to a requested analysis selected from among a plurality of analysis types; assigning at least one centrifugation parameter to each of the first plurality of samples in response to the requested analysis linked to that sample; loading a second plurality of samples into a centrifuge, the second plurality of samples being selected from among the first plurality of samples and comprising samples that have been assigned at least two different centrifugation parameters; determining a centrifugation parameter of highest centrifugation intensity from among the at least two different centrifugation parameters assigned to samples in the second plurality of samples; and centrifuging the second plurality of samples according to a centrifugation protocol comprising the centrifugation parameter of highest centrifugation intensity.

10 Claims, 6 Drawing Sheets

(56) References Cited

U.S. PATENT DOCUMENTS

| | | |
|---|---|---|
| 6,390,965 B1 | 5/2002 | Matsushima |
| 2005/0037502 A1 | 2/2005 | Miller |
| 2007/0020764 A1* | 1/2007 | Miller ............... G01N 35/0092 436/45 |
| 2008/0182742 A1 | 7/2008 | Porte |
| 2008/0190857 A1 | 8/2008 | Beretta et al. |

* cited by examiner

AUTOMATED SAMPLE WORKCELL AND METHOD OF OPERATION

CROSS-REFERENCE TO RELATED APPLICATION

This is a divisional application of U.S. patent application Ser. No. 13/077,468, filed on Mar. 31, 2011, which claims priority under 35 U.S.C. §119(a)-(d) to European Patent Application No. 10158946.3, filed in the European Patent Office on Apr. 1, 2010, and entitled "A Computer-Implemented Method for Operating an Automated Sample Workcell." The entire disclosures of both of the foregoing applications are hereby incorporated by reference.

TECHNICAL FIELD

The present disclosure relates to automated sample workcells and methods of operation that allow the centrifugation of samples having different centrifugation parameters within the same centrifuge.

BACKGROUND

In analytical laboratories and, in particular, clinical laboratories, a multitude of analyses on biological samples are executed in order to determine physiological and biochemical states of patients, which may be indicative of disease, nutrition habits, drug effectiveness, or organ function.

Biological samples used in those analyses may comprise a number of different biological fluids, including, but not limited to, blood, urine, cerebral-spinal fluid, saliva, etcetera. These original biological samples may be processed prior to the analysis. Often the samples are collected in vials which already contain additional substances (e.g., citrate buffer, EDTA buffer, and/or fluids forming a barrier during centrifugation).

Before an analysis can actually be carried out on a biological sample, it is usually necessary to perform a set of pre-analytical steps on the sample. These pre-analytical steps may include, for example, unloading a sample from a sample input station, diluting or concentrating the sample, capping or de-capping the sample, aliquoting the sample, supplementing the sample with various buffers, media and substances, or centrifuging the sample or an aliquot thereof to separate sample constituents. For safety reasons, as well as for reasons of analytical quality, reproducibly, and efficiency, a growing number of such pre-analytical steps and procedures are executed automatically by automated sample workcell systems, also known as "automated pre-analytical systems."

PCT International Publication No. WO 2017/018897 describes a method for processing chemistry and coagulation tests automatically in a laboratory workcell system comprising multiple analyzers and a centrifuge. For the centrifuge, a current centrifuge operation protocol is established. Patient samples are classified at the input station of an automated clinical workcell system and treated differently according to their pre-analysis centrifuging requirements. If a sample has centrifuging requirements which match the currently established centrifuge operating protocol, the sample is loaded into the centrifuge, centrifuged according to the established centrifuge operating protocol, and then forwarded to an appropriate analyzer. If a sample does not have centrifuging requirements which match the currently established centrifuge operating protocol, the sample is retained at the input station until the centrifuge operating protocol is changed appropriately. After the change of the centrifuge operating protocol is completed, the sample is loaded into the centrifuge and centrifuged according to the new operating protocol. According to the disclosed method, only samples requiring the same centrifugation protocol can be centrifuged at the same time in the centrifuge.

U.S. Patent Publication No. 2015/0037503 describes a method for automatically operating a sample handling system to conduct assays on a number of patient samples by comparing the assays to be conducted with a set of defined assay rules. A set of analyzers that are part of the sample handling system are subdivided into analyzers that are in compliance with the defined assay rules and analyzers that not in compliance with the set of defined assay rules. If necessary, at least one analyzer is brought into compliance with defined assay rules of an assay to be conducted on a set of patient samples. The patient samples are then supplied to the analyzer being in compliance with defined assay rules.

U.S. Pat. No. 5,865,718 describes a system and method for operating one or multiple centrifuges using a protocol record database. The user can search the database for the centrifugation protocol necessary for a particular specimen or type of separation desired.

While the foregoing systems and methods have increased the degree of automation of sample handling workflows, several aspects of processing samples are still not flexible enough for many tasks of clinical diagnostics, including the simultaneous centrifugation of samples requiring different centrifugation protocols. As a consequence, centrifugation times of current pre-analytical systems are too long, the sample turnaround numbers are too low, and/or a multitude of centrifuges are necessary to guarantee fast processing of samples requiring different centrifugation protocols by using multiple centrifuges in parallel, which significantly increases the cost of pre-analytical systems.

SUMMARY

The present invention comprises one or more of the features recited in the appended claims and/or the following features, alone or in any combination.

According to one aspect, a method may comprise receiving a first plurality of samples, each of the first plurality of samples being linked to a requested analysis selected from among a plurality of analysis types; assigning at least one centrifugation parameter to each of the first plurality of samples in response to the requested analysis linked to that sample; loading a second plurality of samples into a centrifuge, the second plurality of samples being selected from among the first plurality of samples and comprising samples that have been assigned at least two different centrifugation parameters; determining a centrifugation parameter of highest centrifugation intensity from among the at least two different centrifugation parameters assigned to samples in the second plurality of samples; and centrifuging the second plurality of samples according to a centrifugation protocol comprising the centrifugation parameter of highest centrifugation intensity.

In some embodiments, assigning at least one centrifugation parameter to each of the first plurality of samples may comprise assigning at least one centrifugation parameter of higher centrifugation intensity to each sample linked to a requested coagulation analysis and assigning at least one centrifugation parameter of lower centrifugation intensity to each sample linked to a requested clinical chemistry analysis. In such embodiments, loading the second plurality of samples into the centrifuge may comprise loading at least one sample linked to a requested coagulation analysis into the centrifuge and loading at least one sample linked to a requested clinical chemistry analysis into the centrifuge. Loading the second plurality of samples into the centrifuge may comprise loading each sample in the first plurality of samples into the centrifuge as each sample in the first plurality of samples is received.

In other embodiments, the method may further comprise collecting samples from the first plurality of samples that are assigned a first centrifugation parameter in a first buffer area; collecting samples from the first plurality of samples that are assigned a second centrifugation parameter in a second buffer area, the second centrifugation parameter being different from the first centrifugation parameter; and determining whether a termination condition is fulfilled prior to loading the second plurality of samples into the centrifuge. In such embodiments, loading the second plurality of samples into the centrifuge may comprise loading samples collected in the first buffer area into the centrifuge and loading samples collected in the second buffer area into the centrifuge to fill one or more unoccupied centrifuge buckets remaining after loading the samples collected in the first buffer area.

In some embodiments, collecting samples in the second buffer area may comprise collecting samples that are received with greater frequency than samples collected in the first buffer area. In other embodiments, collecting samples in the second buffer area may comprise collecting samples that are assigned a centrifugation parameter of lower centrifugation intensity than the first centrifugation parameter assigned to samples collected in the first buffer area. Determining wherein determining whether the termination condition is fulfilled may comprise one of determining whether a predefined period of time has elapsed, determining whether a particular time of day has occurred, determining whether a predefined number of samples have been collected in the first buffer area, determining whether a predefined number of samples have been collected in both the first and second buffer areas, and determining whether an explicit centrifugation command has been received.

In still other embodiments, the method may further comprise logically classifying the first plurality of samples into a plurality of classes of compatible centrifugation parameters, each of the plurality of classes of compatible centrifugation parameters including a superior centrifugation parameter and one or more subordinate centrifugation parameters, wherein the second plurality of samples are selected from among one of the plurality of classes of compatible centrifugation parameters. Assigning at least one centrifugation parameter to each of the first plurality of samples may comprise reading an indicator on each of the first plurality of samples to obtain information regarding the requested analysis linked to that sample and processing the obtained information using a rules engine.

According to another aspect, an automated sample workcell may comprise a centrifuge, a sample conveyor, and a controller configured to (i) assign at least one centrifugation parameter to each sample received by the workcell in response to a requested analysis linked to that sample, (ii) operate the sample conveyor to load at least two samples received by the workcell into the centrifuge, the at least two samples including samples that have been assigned at least two different centrifugation parameters, (iii) determine a centrifugation parameter of highest centrifugation intensity from among the at least two different centrifugation parameters, and (iv) operate the centrifuge according to a centrifugation protocol comprising the centrifugation parameter of highest centrifugation intensity.

In some embodiments, the controller may be configured to assign at least one centrifugation parameter of higher centrifugation intensity to each sample linked to a requested coagulation analysis and to assign at least one centrifugation parameter of lower centrifugation intensity to each sample linked to a requested clinical chemistry analysis. In still other embodiments, the automated sample workcell may further comprise a parameter assignment module configured to read an indicator on each sample received by the workcell to obtain information regarding the requested analysis linked to that sample and process the obtained information using a rules engine to determine the at least one centrifugation parameter to be assigned to each sample.

In still other embodiments, the automated sample workcell may further comprise a first buffer area where samples assigned a centrifugation parameter of higher centrifugation intensity a first centrifugation parameter are collected and a second buffer area where samples assigned a centrifugation parameter of lower centrifugation intensity are collected. The controller may be further configured to determine whether a termination condition is fulfilled prior to operating the sample conveyor to load the at least two samples into the centrifuge. In such embodiments, the controller may be configured to operate the sample conveyor to load samples collected in the first buffer area into the centrifuge and operate the sample conveyor to load samples collected in the second buffer area into the centrifuge to fill one or more unoccupied centrifuge buckets remaining after the samples collected in the first buffer area are loaded.

According to yet another aspect, one or more non-transitory, machine-readable media may comprise a plurality of instructions that, in response to being executed, result in a processor assigning at least one centrifugation parameter to each sample received by an automated sample workcell in response to a requested analysis linked to that sample; controlling a sample conveyor to load at least two samples received by the automated sample workcell into a centrifuge, the at least two samples including samples that have been assigned at least two different centrifugation parameters; determining a centrifugation parameter of highest centrifugation intensity from among the at least two different centrifugation parameters; and controlling the centrifuge according to a centrifugation protocol comprising the centrifugation parameter of highest centrifugation intensity.

In some embodiments, the plurality of instructions may further result in the processor assigning at least one centrifugation parameter of higher centrifugation intensity to each sample linked to a requested coagulation analysis and assigning at least one centrifugation parameter of lower centrifugation intensity to each sample linked to a requested clinical chemistry analysis. In such embodiments, the plurality of instructions may further result in the processor controlling a sample conveyor to load at least one sample linked to a requested coagulation analysis into the centrifuge and controlling a sample conveyor to load at least one sample linked to a requested clinical chemistry analysis into the centrifuge. In other embodiments, the plurality of instructions may further result in the processor logically classifying the samples received by the automated sample workcell into a plurality of classes of compatible centrifugation parameters, each of the plurality of classes of compatible centrifugation parameters including a superior centrifugation parameter and one or more subordinate centrifugation parameters, and selecting the at least two samples to be loaded into the centrifuge from among one of the plurality of classes of compatible centrifugation parameters.

BRIEF DESCRIPTION OF THE DRAWINGS

The apparatus, systems, and methods described herein are illustrated by way of example, and not by way of limitation, in the accompanying figures. For simplicity and clarity of illustration, elements illustrated in the figures are not necessarily drawn to scale. For example, the dimensions of some elements may be exaggerated relative to other elements for clarity. The detailed description particularly refers to the following figures in which.

DETAILED DESCRIPTION OF THE DRAWINGS

Figure 1:
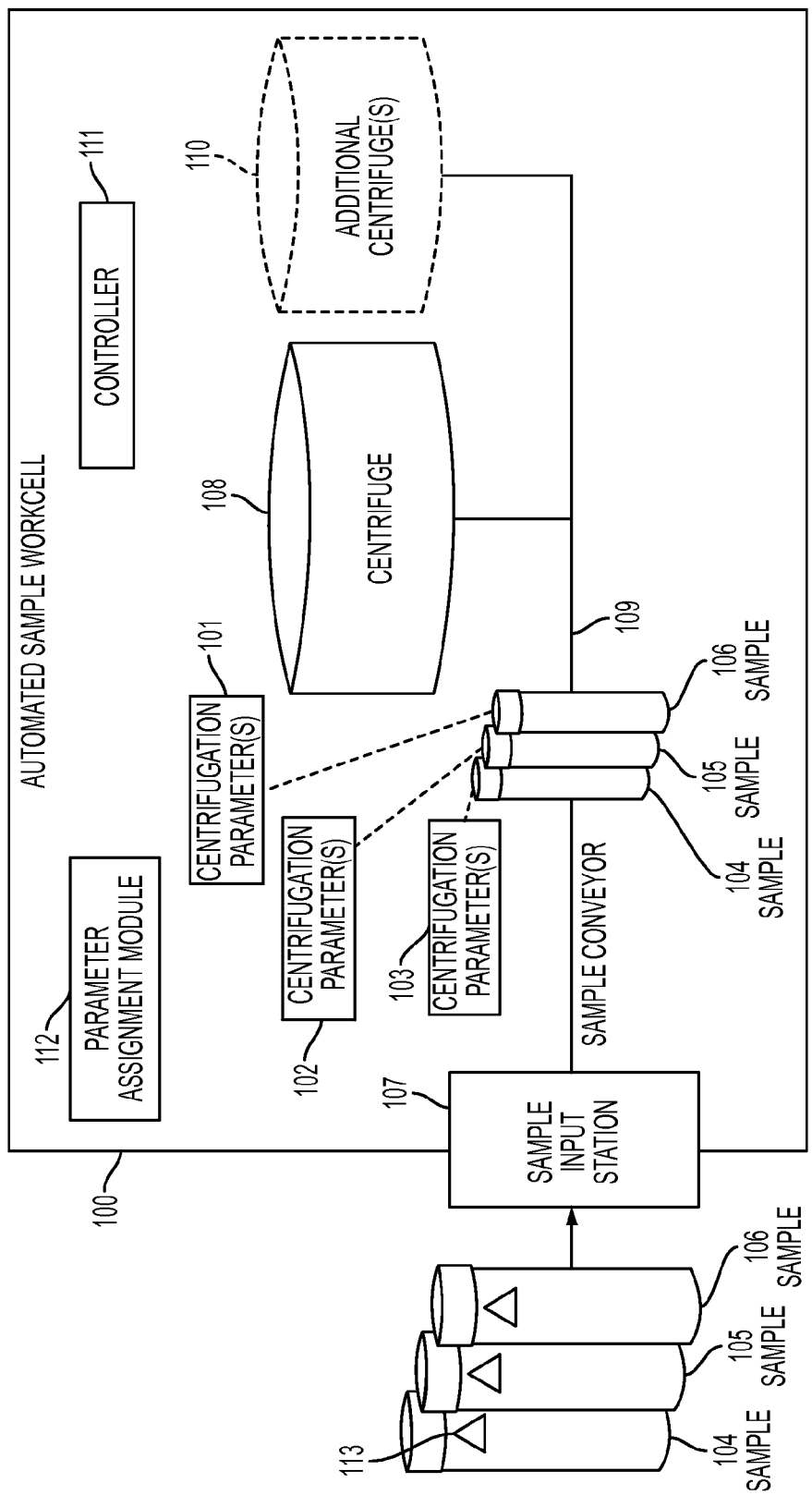
FIG. 1 illustrates a block diagram of one embodiment of an automated sample workcell system comprising a centrifuge.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

In the following description, numerous specific details such as logic implementations and types and interrelationships of system components may be set forth in order to provide a more thorough understanding of the present disclosure. It will be appreciated, however, by one skilled in the art that embodiments of the disclosure may be practiced without such specific details. In other instances, control circuits and full software instruction sequences may have not been shown in detail in order not to obscure the disclosure. Those of ordinary skill in the art, with the included descriptions, will be able to implement appropriate functionality without undue experimentation.

References in the specification to "one embodiment," "an embodiment," "an illustrative embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Some embodiments of the disclosure may be implemented in hardware, firmware, software, or any combination thereof. Embodiments of the disclosure implemented in an automated sample workcell system may include one or more bus-based interconnects between components and/or one or more point-to-point interconnects between components. Embodiments of the disclosure may also be implemented as instructions stored on one or more non-transitory, machine-readable media, which may be read and executed by one or more processors. A non-transitory, machine-readable medium may include any tangible mechanism for storing or transmitting information in a form readable by a machine (e.g., a computing device). For example, a non-transitory, machine-readable medium may include read only memory (ROM), random access memory (RAM), magnetic disk storage media, optical storage media, flash memory devices, and other tangible media.

The present disclosure relates to automated sample workcells and methods of operation that allow the centrifugation of samples having different centrifugation parameters within the same centrifuge. The option to simultaneously centrifuge samples having different centrifugation requirements is advantageous, as no dedicated centrifuge is needed for each particular centrifugation protocol. This reduces the number of centrifuges required and, thereby, reduces the costs of the automated sample workcell system. Compared to automated sample workcell systems that sequentially centrifuge samples having different centrifugation requirements in only one centrifuge, which is often not loaded to its full capacity, the time required to centrifuge all samples is reduced.

Automated sample workcell systems ("workcell systems") are often highly complex systems comprising a multitude of different laboratory apparatus connected by one or more sample conveyors. In addition, workcell systems may comprise pre-analytical sample processing units, such as centrifuges, capping and de-capping units, or aliquoting units, by way of example. Samples may be transported automatically or manually from a pre-analytical processing unit to an analyzer. A variety of analyzers are known in the art that differ from one another, for example, in the types of reagents used, in the number and type of biological samples that can be analyzed in a unit of time, in the analytical approach, etcetera.

One illustrative use of a workcell system according to the present disclosure is the centrifugation of patient samples (e.g., whole blood samples) to prepare those samples for desired types of analysis. Blood flows throughout the whole body, carrying nutrients to the organs as well as waste products to excretory systems. For these reasons, many medical conditions have an effect on the components of blood, and blood tests are among the most commonly performed clinical analyses. Most routine analyses are performed on plasma or serum samples instead of whole blood samples because the cellular components of the blood interfere with some analytical tests. Serum and plasma can be frozen or cooled and, thus, can be stored for several days or weeks for subsequent analysis. Therefore, it is common practice to centrifuge whole blood samples in order to separate plasma or serum from blood cells before the plasma or serum is stored or analyzed.

Blood plasma is the liquid component of blood lacking blood cells. It is mostly water and typically contains dissolved proteins, glucose, clotting factors, mineral ions, and hormones. Blood plasma is prepared by spinning whole blood samples containing anti-coagulant substances in a centrifuge until the blood plasma is separated from the blood cells at the bottom of the tube.

Blood serum is blood plasma without fibrinogen or other clotting factors. It typically includes the proteins not used in blood clotting, electrolytes, antibodies, antigens, and hormones, as well as exogenous substances like drugs. Blood serum is commonly used for a broad variety of analyses, such as analyses for the detection of antibodies, for blood typing, or for DNA analytics in a forensic laboratory. Analyses are laboratory procedures characterizing a parameter of a biological sample (e.g., its opacity) or of an analyte of the biological sample. An analyte is a component of a sample to be analyzed (e.g., molecules of various sizes, ions, proteins, metabolites and the like). The gathered information may be used to evaluate the impact of the administration of drugs on the organism, or on particular tissues, or to make a diagnosis, by way of example. The determination of analytes and their concentrations within a biological sample is often referred to as "clinical chemistry" in the context of blood sample analysis. The characterization of the cellular components of a blood sample is often called "clinical hematology," while laboratory analyses evaluating a blood sample's clotting mechanism are referred to as "coagulation analyses."

The clotting of a blood sample may make clinical chemistry analyses impossible or result in erroneous measurement values. Therefore, for those kinds of analyses, clotting is prevented by adding anticoagulant substances to the blood sample immediately after the sample is obtained from the patient. Anticoagulant substances include sodium citrate, EDTA, heparin, and others. Some vials used for collecting whole blood samples may contain such anticoagulant substances.

Alternatively, in cases where serum is to be obtained from a whole blood sample, the sample tube may contain substances which initiate and accelerate clotting. These so-called "clot activators" accelerate the clotting of fibrinogen, blood cells, and other clotting factors. Blood cells and other clotting factors may then be separated from the sample by centrifugation after the completion of the clotting process.

As the sample tubes used to collect blood often contain additional substances (e.g., anticoagulant substances or clot activators) which have an impact on the processing of the sample, a mix-up of sample tube types can make a blood sample unusable for analysis. For example, sample tubes provided by some manufacturers are adapted for pre-analytical and analytical requirements of a particular analysis (e.g., a clinical chemistry analysis, a hematological analysis, or a coagulation analysis). To prevent errors in the collection and handling of samples, many manufacturers encode the cap color of sample tubes according to a fixed color scheme corresponding to the type of analysis for which each sample tube is adapted. Table 1 contains an illustrative list of sample tube types I-VII, with each illustrative sample tube type containing a particular set of substances and being optimized for the preparation of samples according to one or more types of analyses.

TABLE 1

| Sample Tube Type | Added Substances | Sample Type | Possible Analyses |
|---|---|---|---|
| I | Clot Activator | Serum Sample | Clinical Chemistry on Serum (e.g., determining glucose/ion/protein level); Immunology; Routine Blood Donor Screening; Diagnostic Testing for Infectious Diseases |
| II | Clot Activator Gel (gel density is between density of blood serum and of blood cells; assists in separating serum and blood cells after centrifugation; prevents substance exchange between serum and blood cells) | Serum Sample | Clinical Chemistry on Serum (e.g., determining glucose/ion/protein level); Immunology; Routine Blood Donor Screening; Diagnostic Testing for Infectious Diseases |
| III | Anticoagulant EDTA (K2-EDTA does not distort blood cells and is therefore preferred anticoagulant for hematological analyses) | Hematological Samples (Whole Blood) | Clinical Hematology Examinations of Blood Cells; Routine Blood Donor Screening |
| IV | Anticoagulants Heparin, Lithium, Heparin, and Sodium Gel (gel density is between density of blood plasma and of blood cells; assists in separating plasma and blood cells after centrifugation; prevents substance exchange between plasma and blood cells) | Plasma Sample | Clinical Chemistry on Plasma (e.g., determining glucose/ion/protein level); Immunology; Routine Blood Donor Screening; Diagnostic Testing for Infectious Diseases; Some Items of Hemorrheology |
| V | Thrombin (rapid clot activator) | STAT Serum Sample | Rapid Serum Analysis |
| VI | Anticoagulant Citrate (binds the calcium of the blood sample) | Citrate-Plasma Sample | Coagulation Analyses (adding calcium allows blood to clot again); Platelet Function Assays |
| VII | | Urine Sample | Chemical Analysis |

Commonly, manufacturers of sample tubes also provide their customers with information on recommended centrifugation protocols which are considered as optimum centrifugation protocols to prepare a particular sample for a desired analysis. As used in the present disclosure, a "centrifugation protocol" is a set of instructions controlling the operation of a centrifuge according to one or more centrifugation parameters. A "centrifugation parameter" specifies one or more operational parameters of a centrifuge. A centrifugation parameter may include, but is not limited to, a centrifugal force, a centrifugation time, an acceleration time, a ramp-up time, a deceleration time, or a temperature in a centrifuge. Table 2 sets forth illustrative centrifugation parameters for certain illustrative sample tube types (e.g., those recommended by a manufacturer of the sample tube).

TABLE 2

| Sample Tube Type | Recommended Centrifugation Parameters |
|---|---|
| II | Centrifugal Force: 2000 g Centrifugation Time: 5 min |
| IV | Centrifugal Force: 2000 g Centrifugation Time: 5 min |
| VI | Centrifugal Force: 3000 g Centrifugation Time: 10 min |
| VII | Centrifugal Force: 1200 g Centrifugation Time: 10 min |

A centrifuge operates according to a particular centrifugation protocol by spinning a rotor containing one or more samples at a particular speed resulting in a particular centrifugal force for a particular time at a particular temperature, as specified by the centrifugation parameters of the centrifugation protocol. According to the present disclosure, at least one centrifugation parameter is assigned to each sample processed by the workcell system. When a centrifuge is set to operate at a specific speed, for example, centrifugation intensity may be varied by choosing different centrifugation durations (e.g., 5 minutes for samples undergoing a clinical chemistry analysis and 10 minutes for samples undergoing a coagulation analysis). In many practical cases, however, a particular centrifugation parameter would invoke a centrifugation protocol which comprises a particular speed or force and a particular duration. Each centrifugation protocol may further comprise a ramp-up of the centrifugation speed, or even centrifugation at different speeds with the same samples loaded.

The centrifugation parameters which primarily determine the centrifugation intensity are the centrifugation speed, or centrifugal force, and the centrifugation time. In the context of centrifuging samples in a laboratory, the terms "centrifugation speed" and "centrifugal force" are often used synonymously as the centrifugal force can be calculated from a given centrifugation speed, and vice versa. A centrifugal force is executed on a body (e.g., a biological sample in a centrifuge bucket) if the body is moving in a circular path (i.e., is centrifuged around a fixed axis). The centrifugal force pushes the body away from the center of the circular path. The higher the centrifugation speed of the centrifuge, usually measured in revolutions per minute (rpm) or in meters per second (m/s), the higher the centrifugal force executed on the centrifuged body. The unit revolutions per minute indicates the number of turns a centrifuge performs per unit of time (e.g., within a minute). The unit meters per second indicates the length of a path a centrifuged sample travels along a circle around the axis of a centrifuge, where the radius of the circle is typically the radius of the centrifuge rotor or the distance between the centrifuge bucket and the axis of the centrifuge. The magnitude of the centrifugal force (F) given a particular centrifugation speed (v) is given by the formula $F=mv^2/r$, where m is the mass of the body (e.g., the sample, in kilograms), v is the speed of the body (in m/s), and r is the radius of the centrifuge (in meters). Alternatively, the magnitude of the centrifugal force is given by $F=m\omega^2 r$, where $\omega$ is the angular velocity of the centrifuge.

Coagulation analyses require higher centrifugation intensities than clinical chemistry analyses, because the number of cells or particles that may acceptably remain in the plasma for coagulation analyses is smaller than for clinical chemistry analyses. As mentioned above, the centrifugation intensity is a value which is primarily determined by the centrifugal force, the centrifugation time, or by a combination of both parameters. According to the present disclosure, it is not necessary to determine exact centrifugation intensities. Rather, only the relative centrifugation intensities of samples loaded, or to be loaded, into the centrifuge need be compared.

A centrifugation parameter, or protocol, of "highest centrifugation intensity" may be determined by comparing all centrifugation parameters that have been assigned to the samples loaded into the workcell system with one another. For instance, the centrifugation parameter of highest centrifugation intensity may be the centrifugation time of the sample having the longest assigned centrifugation time, provided the assigned centrifugal forces of the samples are equal. Analogously, the centrifugation protocol of highest centrifugation intensity may be the centrifugation protocol based on the centrifugation parameters of the sample having the longest assigned centrifugation time, provided the assigned centrifugal forces of the samples are equal. Alternatively, the centrifugation parameter of highest centrifugation intensity may be the centrifugal force of the sample having the highest assigned centrifugal force value, provided the assigned centrifugation times of the samples are equal. Likewise, the centrifugation protocol of highest centrifugation intensity may be the centrifugation protocol based on the centrifugation parameters of the sample having the highest assigned centrifugal force value, provided the assigned centrifugation times of the samples are equal.

In cases where a first sample has a longer assigned centrifugation time than a second sample, while the second sample has a higher assigned centrifugal force value than the first sample, it may be determined experimentally which of those parameters should be considered the centrifugation parameter of highest centrifugation intensity and which centrifugation parameters constitute the centrifugation protocol of highest centrifugation intensity. Alternatively, a person skilled in the art may decide, based on his or her experience and knowledge, which centrifugation parameter should be considered the parameter of highest centrifugation intensity.

In illustrative embodiments of the present disclosure involving blood sample analysis, centrifugation time is treated as the centrifugation parameter of highest centrifugation intensity and is used to determine the centrifugation protocol according to which both serum samples and coagulation samples are simultaneously processed within the same centrifuge. As a result, serum samples may be centrifuged for a longer time, if they are loaded into the centrifuge together with coagulation samples. The overall turnover time of the workcell system, however, is reduced.

The time at which the comparison of centrifugation parameters of different samples is executed may vary in different embodiments. In some illustrative embodiments, the comparison of centrifugation parameters may be executed after loading the samples into the centrifuge. In other illustrative embodiments, the comparison of centrifugation parameters may be executed during the process of loading the samples into the centrifuge. These embodiments have the advantage of guaranteeing that all samples loaded into the centrifuge are compatible with the centrifugation protocol of highest centrifugation intensity. According to still other illustrative embodiments, the comparison of centrifugation parameters assigned to the samples loaded into the workcell system is executed before the samples are loaded into the centrifuge. These embodiments also have the further advantage of allowing samples to be directed to different buffer areas of the workcell system.

A clinical laboratory may need to execute a multitude of analytical tests on a multitude of blood samples collected in different sample tube types, according to different optimum centrifugation protocols each day. Typically, the sequence and number of analytical tests, as well as the requested centrifugation protocols, will not be known in advance. In addition, certain samples may need to be urgently processed and analyzed, as the analysis results may be of life-crucial importance for a patient (i.e., "STAT" samples). In a clinical laboratory associated with, for example, a hospital, the design of a workcell system which is capable of flexibly centrifuging any type of sample according to its respective centrifugation protocol for a particular analysis, as well as being operable to preferentially process STAT samples, is a highly complex task.

Although Table 1 contains an illustrative list of "sample tube types," the type of sample is not determined or characterized by the tube it is contained in but, rather, by the type of analysis requested for the sample. Thus, a serum sample is a blood sample for which a clinical chemistry or immunology analysis was requested and from which serum is to be prepared prior to the requested analysis. A plasma sample is a blood sample for which a clinical chemistry or immunology analysis was requested and from which plasma is to be prepared prior to the requested analysis. A coagulation sample is a blood sample for which a coagulation test was requested. A STAT serum sample is a blood sample for which a rapid clinical chemistry or immunology analysis was requested and for which a short preparation time is needed. In some cases, blood samples are collected from a patient after a particular analysis has been requested or in the knowledge that a particular analysis will be requested in the future. Accordingly, the blood may be collected in sample tubes specially adapted to prepare serum or plasma for the requested type of analysis (e.g., the illustrative sample tube types of Table 1). In other cases, however, the same sample tube type may be used for different types of samples. In any case, the centrifugation parameter assigned to a sample depends on the requested analysis. In embodiments where the sample tube type is a clear indicator of the type of analytical procedure requested for the contained sample, the sample tube type may be used to determine the one or more centrifugation parameters to be assigned.

It is generally understood that, if a blood sample is centrifuged for a longer time or with a higher centrifugal force than recommended for a particular kind of analysis, the quality of the analysis may be negatively affected. One possible reason is that the cell membranes of blood cells may be damaged, resulting in hemolysis, an effect which negatively interferes with several analytical tests. Another possible reason is that the gel barrier used to separate the serum/plasma from the clot/cells may be destroyed by a centrifugation of higher intensity. The present disclosure is based upon the unexpected observation that, for several types of samples and sample tubes, a deviation from the recommended centrifugation protocol within a particular intensity range does not have negative consequences on the quality of the analysis. Furthermore, sample tubes designed for use at lower centrifugation intensities may be used at higher centrifugation intensities without destruction of the tubes.

Using the observation that a centrifugal force normally employed with coagulation samples does not have a negative impact on the quality of other types of blood analysis, the present disclosure teaches an improved automated sample workcell system that allows the simultaneous centrifugation of multiple samples to be used in different analyses, and thus requiring different centrifugation protocols, within the same centrifuge. Although the principles of the present disclosure are described in the context of blood sample analysis, the described embodiments are merely illustrative of those principles. Persons of skill in the art will understand that numerous modifications may be made regarding the type of biological sample to be centrifuged (e.g., urine, saliva, cerebral spinal liquor, etc.), regarding the centrifugation parameters applicable to a particular type of sample, and regarding the kind of analytical test for which a sample is prepared.

Automated sample workcell systems according to the present disclosure may reduce the overall time needed to prepare samples for analysis. The workcell systems disclosed herein may avoid situations in which a centrifuge is not loaded to its full capacity (with samples having a particular centrifugation protocol) while other samples having a different centrifugation protocol must wait in a buffer area of the workcell. In some embodiments, a centrifuge having only a fraction of its buckets occupied by samples requiring a centrifugation protocol of higher centrifugation intensity can be filled to capacity with samples requiring a centrifugation protocol of lower centrifugation intensity. In other embodiments, a centrifuge having only a fraction of its buckets occupied by samples requiring a centrifugation protocol of lower centrifugation intensity can be filled to capacity with samples requiring a centrifugation protocol of higher centrifugation intensity.

In one illustrative embodiment, a centrifuge having only a fraction of its buckets occupied by coagulation samples (Type VI sample tube) can be filled to capacity with blood samples to be used for other analytical tests (e.g., clinical chemistry analyses). In general, coagulation analyses are not as frequently requested as clinical chemistry analyses, and the option to load samples of other types into centrifuges using a coagulation centrifugation protocol is therefore of significant practical relevance and economic impact. Moreover, by centrifuging samples having different centrifugation protocols within the same centrifuge, the number of centrifuges in the system can be reduced.

Some illustrative embodiments of the workcell system may include a sample conveyor which connects a sample input station to at least one centrifuge. As used herein, the term "conveyor" includes any kind of conveyor belt, robotic arm, or other device that is operable to transport samples from the sample input station to the at least one centrifuge, so that the samples may be loaded into the centrifuge. In some embodiments, the sample input station may be incorporated as part of the at least one centrifuge of the workcell system. In such embodiments, the conveyor may also be a component of the at least one centrifuge, transporting samples from the sample input station of the centrifuge to the centrifuge buckets.

The sample input station receives samples to be prepared for particular requested analyses. Each sample may be marked by a unique identifier (e.g., a bar code, a matrix code, or the combination of a unique sample rack code and a unique position of the sample within the sample rack). At least one centrifugation parameter is assigned to each sample. Depending on the embodiment, this assignment may be executed within the workcell system or may be executed on the sample in advance (before the sample is loaded into the automated sample workcell system). In some embodiments, the at least one centrifugation parameter is assigned to the each sample when an analysis request is entered into a data management system, before the samples are loaded into the workcell system. The data management system may automatically assign the at least one centrifugation parameter in accordance with one or more analytical tests specified in the analysis request. For example, if a coagulation test is requested, the data management system would assign centrifugation parameters adapted to prepare a sample for coagulation analysis to the requested sample(s).

A single analysis request for a particular patient may contain requests for clinical, immunological, and coagulation tests. Typically, blood is drawn from the patient into different sample tubes (e.g., one tube for clinical chemistry and immunological testing and one tube for coagulation testing). These tubes may be marked with the same patient-specific barcode. Accordingly, the workcell system may need to distinguish these tubes (with the same patient barcode), which can be done using a marking on the tube indicating tube type (e.g., the tube closure). The workcell system may then assign centrifugation parameters automatically to the sample tubes according to the analytical tests requested. It will appreciated that centrifugation parameters might also be assigned to samples manually (e.g., by the operator of the sample workcell).

In some embodiments, the assignment of at least one centrifugation parameter may be executed automatically by a "parameter assignment module" when each sample is received by the sample input station of the workcell system. The parameter assignment module may be implemented in the form of a rules engine or some other computer-implemented process. For instance, each assignment may be stored as an entry in a database connecting a sample identifier with one or more centrifugation parameters.

The assignment of one or more centrifugation parameters to a sample may depend on information contained in an analysis request (i.e., an order or request to execute a particular type of analysis on a particular sample) received by the workcell system. An analysis request may be entered manually (e.g., by submitting an electronic or paper-based form). An analysis request may be entered directly into the workcell system via a man-machine interface (e.g., a keyboard, a touch screen, or a remote computer). In some embodiments, an analysis request may be managed and transferred to the workcell system by a laboratory's middleware or information system. Additionally or alternatively, the assignment of one or more centrifugation parameters to a sample may depend on information read from a label or a cap of each sample. In some embodiments, the color of the sample cap or the label on the sample (e.g., a bar code) may be read and used as an indicator of the at least one centrifugation parameter to be assigned to the sample.

The parameter assignment module may determine whether data contained in an analysis request or a sample label fulfills one or more conditions and may assign one or more centrifugation parameters in dependence on the results (i.e., a "rules engine"). For example, one condition that could be applied to an analysis request might be whether the type of the requested analysis is equal to a particular analysis type (e.g., a coagulation test). If the condition is fulfilled and, for example, a coagulation test was requested for the sample, the sample of is assigned a set of centrifugation parameters comprising a centrifugal force of 3000 g and a centrifugation time of 10 minutes. Likewise, the condition could be applied on data read out from the label of a sample (e.g., the sample tube type). As another example, if the condition that a received sample is Type VII (i.e., a urine sample) is fulfilled, then one or more centrifugation parameters for a urine sample are assigned.

In some embodiments, the assignment of at least one centrifugation parameter to a sample may also include a determination of whether a sample has already been centrifuged. This information may be retrieved by the workcell system from a laboratory information system (LIS), from a software module that is part of the laboratory middleware, or from a standalone software application designed for managing data associated with the processing and analysis of biological samples. This check may be used to ensure that a sample is not unnecessarily centrifuged a second time, which helps to save centrifugation resources.

In some embodiments, multiple centrifugation parameters may be assigned to each sample (e.g., a particular centrifugation time and a particular centrifugal force). The one or more centrifugation parameters assigned to each sample may be derived from a set of recommended centrifugation parameters provided by a manufacturer of the sample tubes, may be based on the technical knowledge and experience of the laboratory staff, or may be based on values obtained from scientific texts and technical journals. In some embodiments, the centrifugation protocol assigned to each sample may be optimal for a particular analysis, ensuring that the requested analysis can be carried out on the centrifuged sample and will return valid results.

After one or more centrifugation parameters are assigned to each sample, some or all of the received samples may be transported by the sample conveyor to the at least one centrifuge of the workcell system. A controller (e.g., a processor, a software component, or a firmware component) of the workcell system may compare the centrifugation parameters assigned to each of the samples. In most cases (i.e., typical use case scenarios), the samples loaded to the workcell system will have different assigned centrifugation parameters. The controller may determine, as a result of the comparison, the centrifugation parameter(s) of highest centrifugation intensity and/or the centrifugation protocol of highest centrifugation intensity. In various embodiments, the controller may be implemented as an integral component of the workcell system, as a standalone software application, or as a software module integrated with the LIS or the laboratory middleware.

After the controller determines the centrifugation parameter(s) of highest centrifugation intensity, the samples may be loaded into the centrifuge and centrifuged according to the centrifugation protocol including the centrifugation parameter(s) of highest centrifugation intensity. For example, samples received by the sample input station might include (1) whole blood samples used to prepare serum for clinical chemistry and assigned a centrifugal force of 2000 g and a centrifugation time of 5 minutes, (2) whole blood samples used to prepare plasma in Type IV sample tubes and assigned a centrifugal force of 2000 g and a centrifugation time of 5 minutes, and (3) coagulation samples assigned a centrifugal force of 3000 g and a centrifugation time of 10 minutes. In such a scenario, the controller may determine that the centrifugation parameters "centrifugal force=3000 g" and "centrifugation time=10 min" (assigned to the coagulation samples) determine the centrifugation protocol of highest centrifugation intensity. In other scenarios, the controller may determine that the centrifugation protocol of highest centrifugation intensity comprises the centrifugation parameters assigned to serum or plasma samples for clinical chemical analysis (e.g., a centrifugal force of 2000 g and a centrifugation time of 5 minutes). In still other scenarios, the controller may determine that the centrifugation protocol of highest centrifugation intensity comprises the centrifugation parameters assigned to urine samples (e.g., a centrifugal force of 1200 g and a centrifugation duration of 10 minutes).

In some illustrative embodiments, samples are loaded into the at least one centrifuge of the workcell system in the order they are received by the sample input station, or in the order they are transported to the at least one centrifuge by the sample conveyor. When the centrifuge is loaded to capacity, after the elapse of a specified period of time, or when the workcell system receives an explicit command, the centrifuge is operated according to the centrifugation protocol of highest centrifugation intensity, based on the centrifugation parameters of the samples loaded in the centrifuge.

In other illustrative embodiments, the workcell system also includes at least two buffer areas (e.g., a first buffer area and a second buffer area) for collecting samples that are assigned different centrifugation parameters or that differ from each other with regard to their average occurrence frequency. For instance, samples that are assigned one or more centrifugation parameters of higher centrifugation intensity may be collected in a first buffer area, while samples that are assigned one or more centrifugation parameters of lower centrifugation intensity (e.g., all other samples) may be collected in a second buffer area. In some embodiments, a sample may be directed to a particular buffer area based on one or more of: the sample type (e.g., blood, urine, etc.), the sample tube type (e.g., Type II, Type VII, etc.), the degree of urgency associated with the sample (e.g., STAT samples), the average frequency of receiving the sample type, the average frequency of receiving the requested type of analysis, and the like.

In one illustrative embodiment, as STAT samples are received by the workcell system, the STAT samples are collected in a first buffer area. All other samples received by the workcell system are collected in a second buffer area and may be used to fill unoccupied buckets of the at least one centrifuge prior to centrifuging the STAT samples. The STAT status of a sample may be determined by data contained in an analysis request.

In another illustrative embodiment, samples with a sample type or with a requested type of analysis that, on average, occurs less frequently are collected in a first buffer area of the workcell system. All other samples received by the workcell system are collected in a second buffer area. The samples collected in the first buffer area may be loaded into the at least one centrifuge of the workcell system after a termination condition is fulfilled. This termination condition may be the elapse of a specified time period, the occurrence of a specified time of day, the collection of a specified number of samples in the first and/or second buffer area, an explicit centrifugation command, etcetera. The termination condition for STAT samples may differ from that of other samples (i.e., the minimum number of STAT samples to be collected in the first buffer area may be smaller than for other sample types and/or the time period before initiating centrifugation may be shorter). If, after loading all samples from the first buffer area, the centrifuge has not been loaded to capacity, samples collected in the second buffer area may be transferred to the unoccupied centrifuge buckets. After the centrifuge is loaded to capacity, or after all available samples have been loaded, the centrifuge is operated according to the centrifugation protocol of highest centrifugation intensity (and/or the centrifugation parameter(s) of highest centrifugation intensity).

By way of example, a workcell system may collect coagulation samples in a first buffer area because they are assigned a centrifugation parameter of higher intensity than clinical chemical analysis samples. In many laboratories, coagulation samples are also processed less frequently than clinical chemistry samples (e.g., Type I and Type II sample tubes). In this example, the clinical chemistry samples are collected in a second buffer area. After a termination condition is fulfilled, the coagulation samples are loaded by the sample conveyor from the first buffer area into the centrifuge. If one or more centrifuge buckets remain unoccupied, clinical chemistry samples are loaded by the sample conveyor from the second buffer area into the centrifuge.

In the foregoing illustrative embodiments, samples contained in any sample tube type (e.g., those listed in Tables 1 and 2) can be centrifuged together according to the centrifugation parameters of highest centrifugation intensity (e.g., "centrifugal force=3000 g" and "centrifugation time=10 min" where coagulation samples are present). In some laboratories, however, there may be sample types or analysis types for which centrifugation at the highest centrifugation intensity could invalidate the analysis results or make the execution of the desired analysis on the sample impossible. For example, EDTA-treated blood samples collected in Type III sample tubes may be used to examine the blood cells (e.g., their shape and number per volume unit). A centrifugation at high intensity could render that analysis impossible.

Thus, in some illustrative embodiments, the controller may also determine whether some samples received by the workcell system are incompatible with the centrifugation parameter of highest centrifugation intensity assigned to the received samples. A sample may be determined to be incompatible with the centrifugation parameter of highest centrifugation intensity if the resulting centrifugation of the sample would result in the invalidation of or a deterioration in the quality of the analysis results or would make the execution of the desired analysis on the samples impossible. Such samples are referred to herein as "incompatible samples." If the controller detects incompatible samples, those samples are prohibited from being loaded into the at least one centrifuge together with samples assigned the centrifugation parameter of highest centrifugation intensity. In some embodiments, incompatible samples may be collected in a third buffer area. After the samples having the centrifugation parameter of highest centrifugation intensity (and any other samples that are not negatively affected) have completed centrifugation, a new centrifugation protocol may be established for the at least one centrifuge, the incompatible samples may be transferred from the third buffer area to the at least one centrifuge by the sample conveyor, and incompatible samples may be centrifuged according to their assigned centrifugation parameters.

The workcell system may also include a second centrifuge. In such embodiments, the incompatible samples may be transferred to the second centrifuge instead of being collected in a third buffer area. A centrifugation protocol determined by the centrifugation parameters assigned to the incompatible samples may be established at the second centrifuge. The incompatible samples may then be centrifuged according to the established protocol.

In some embodiments, the workcell system may be operable to determine its workload or to receive workload information from a user of the system (e.g., the operator). If the workload of the system is low, the controller may process each sample according to its assigned centrifugation parameters. If the workload of the system is high, however, the controller may process samples having different assigned centrifugation parameters together in the same centrifuge (according to the centrifugation protocol of higher centrifugation intensity, as described above). In other words, the workcell system may preferentially employ the methods of operation described herein depending on its workload.

Finally, after the samples have been centrifuged, the samples may be automatically or manually transferred to an analyzer. Alternatively, the samples may be further processed in one or more pre-analytical steps (e.g., de-capping the sample tubes, taking aliquots of the centrifuged sample for subsequent analysis, and, in some cases, also centrifuging the aliquot).

Further embodiments of the present disclosure are particularly suited for usage in laboratories in which a multitude of samples (not necessarily having compatible centrifugation parameters) need to be centrifuged. These embodiments operate based on a logical classification of samples based on their assigned centrifugation parameters. The logical classes of samples may be physically separated. After the samples are classified into these sub-sets, multiple sample sub-sets are grouped together if they have compatible centrifugation parameters. The sample sub-sets having compatible centrifugation parameters are centrifuged together in a first centrifuge, while sample sub-sets having incompatible centrifugation parameters may be centrifuged either in parallel in a second centrifuge or in sequence in the first centrifuge (after the first run has completed).

Illustrative embodiments using such a logical classification system may maintain the compatible centrifugation parameters for particular analyses in the form of database tables, by way of example. Table 3 gives one example of a table containing centrifugation parameters optimized to prepare a biological sample for a particular analysis or group of analyses.

TABLE 3

| ID | Analysis Type | Centrifugation Parameter |
|---|---|---|
| A | Clinical Chemistry Analysis on Serum or Plasma Sample | Centrifugal Force: 2000 g |
| B | Coagulation Testing | Centrifugal Force: 3000 g |
| C | Clinical Chemistry Analysis on Urine Sample | Centrifugal Force: 1200 g |
| D | Hematological Analysis | No Centrifugation |
| E | Separation of Red and White Blood Cells | Centrifugal Force: 10,000 g |

Table 4 gives one example of a table containing classes of compatible centrifugation parameters. Each class (I and II) comprises exactly one superior centrifugation parameter and one or more subordinate centrifugation parameters. A centrifugation parameter can be a superior parameter in one class (parameter A in Class II) and be a subordinate parameter of other classes (parameter A in Class I).

TABLE 4

| Class ID | Superior Centrifugation Parameter | Subordinate Centrifugation Parameter(s) |
|---|---|---|
| I | B | A, C |
| II | A | C |

If the centrifuge of the workcell system is loaded entirely with samples having the same assigned centrifugation parameter (e.g., entirely with clinical chemistry analysis serum or plasma samples assigned parameter A), the centrifugation protocol executed on the samples uses centrifugation parameter A. If the workcell system receives samples that are assigned different centrifugation parameters than one another, only samples having compatible centrifugation parameters (i.e., samples in the same class) are loaded together into the same centrifuge. These samples are then centrifuged according to the superior centrifugation parameter of the class. By way of example, if samples that are assigned parameters A, B, and C are to be centrifuged, these samples are all loaded together into the centrifuge and centrifuged according to centrifugation parameter B (i.e., the superior centrifugation parameter of class I). As another example, if samples that are assigned parameters A and C (but not B) are to be centrifuged, these samples are loaded together into the centrifuge and centrifuged according to centrifugation parameter A (i.e., the superior centrifugation parameter of class II). Alternatively, if samples are assigned a centrifugation parameter that is incompatible with other centrifugation parameters (e.g., parameter E assigned to samples for red/white blood cell separation), those samples are prohibited from being loaded and centrifuged together with other samples (e.g., having parameters A, B, and C).

The workcell system according to the above illustrative embodiment may be operated as follows. First, the sample input station may receive the samples to be centrifuged. The parameter assignment module may then assign at least one centrifugation parameter to each a sample based on the analysis to be executed on the sample. The assignment may depend on data contained in an analysis request or in a label of the sample. The received samples are then logically classified into sample sub-sets according to their assigned centrifugation parameters. Next, the controller determines which sample sub-sets may be grouped as a class of compatible centrifugation parameters. Only samples belonging to a class of compatible centrifugation parameters are transferred to the centrifuge at the same time. If the sample sub-sets can be assigned to different classes, the class of compatible centrifugation parameters comprising the largest number of samples is used. In some embodiments, the centrifugation parameter of highest centrifugation intensity within a class is considered to be the superior centrifugation parameter. If all received samples are assigned the same centrifugation parameter, that parameter is considered to be the superior centrifugation parameter. Finally, a centrifugation protocol is established at the centrifuge in accord with the superior centrifugation parameter of the class loaded into the centrifuge, and the loaded samples are centrifuged according to the established protocol.

In other embodiments, the sample sub-set having the superior centrifugation parameter may be collected in a first buffer area, while the sample sub-set(s) having a subordinate centrifugation parameter may be collected in a second buffer area. After a termination condition is fulfilled, the samples in the first buffer area are transferred to the centrifuge. If any centrifuge buckets are left unoccupied, they are then filled with samples from the second buffer area, provided that such samples are also in the same class (i.e., are compatible with the superior centrifugation parameter). Once loaded, the centrifuge may be operated according to the superior centrifugation parameter.

Referring now to FIG. 1, a block diagram of one illustrative embodiment of an automated sample workcell system 100 is shown. The workcell system 100 comprises a sample input station 107, at least one centrifuge 108, and a sample conveyor 109 for automatically transporting biological samples 104-106 from the sample input station 107 to the at least one centrifuge 108. Some embodiments of the workcell system 100 may further include one or more additional centrifuges 110, which are also connected to the sample input station 107 via the sample conveyor 109. When samples are received by the sample input station 107, a parameter assignment module 112 assigns each sample 104-106 at least one centrifugation parameter 101-103. For example, sample 104 is assigned centrifugation parameter 103, and sample 106 is assigned centrifugation parameter 101. The parameter assignment module 112 may utilize data contained in an analysis request (i.e. an order) or information specified by a label 113 attached to each sample 104-106. The label 113 may be a unique code of the sample (e.g., a bar code, a matrix code, or the combination of a unique sample rack code and a unique position of the sample within the sample rack). The controller 111 is operable to compare the centrifugation parameters 101-103 that are assigned to each sample 104-106 and to determine the centrifugation parameter of highest centrifugation intensity and the corresponding centrifugation protocol of highest centrifugation intensity. Although the controller 111 and the parameter assignment module 112 are shown as distinct components in FIG. 1, it is contemplated that the controller 111 may perform both of these functions. After the sample conveyor 109 loads the samples 104-106 into the centrifuge 108, the samples 104-106 may be centrifuged according to the centrifugation protocol of highest centrifugation intensity.

Figure 2:
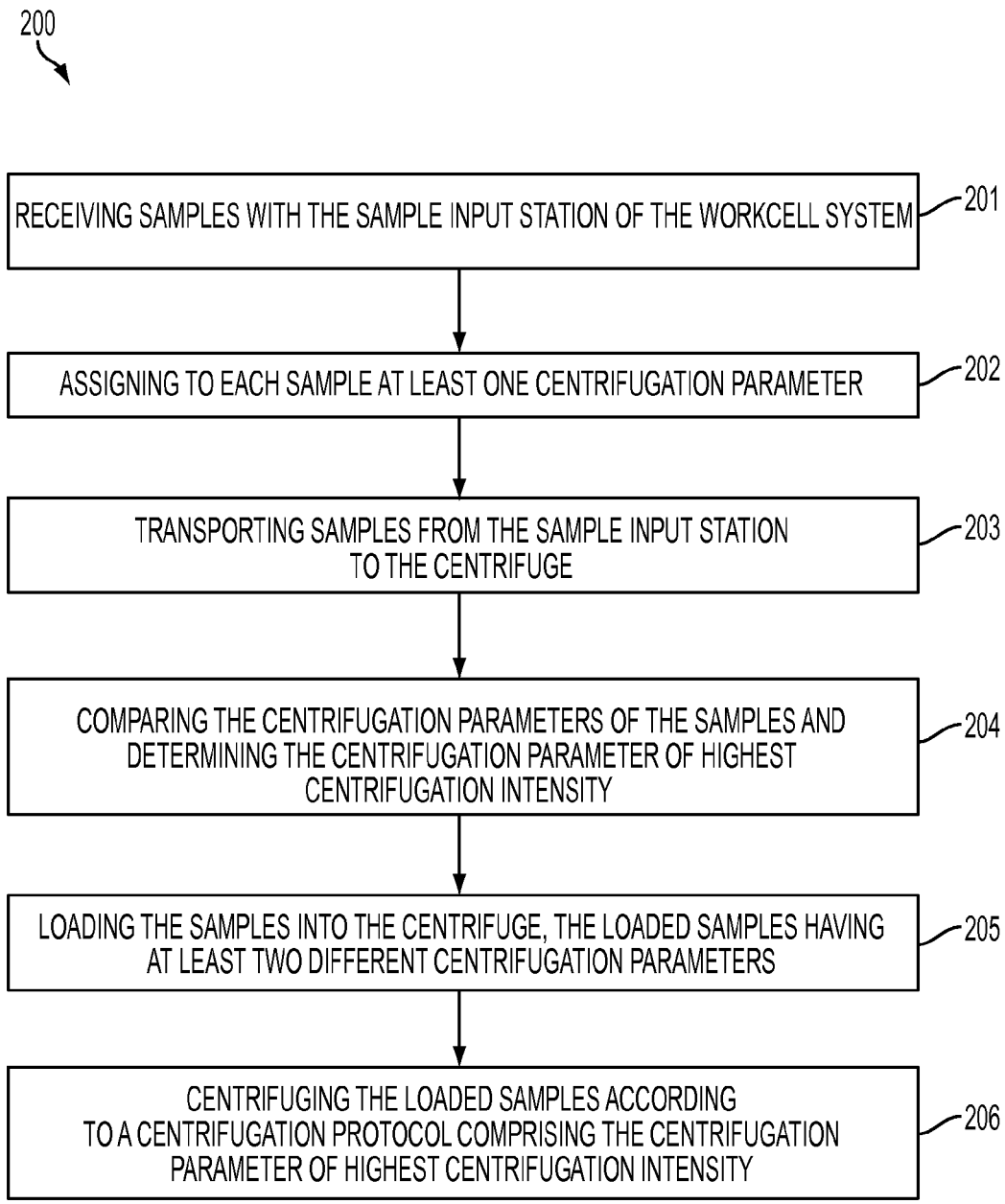
FIG. 2 illustrates a flowchart of one embodiment of a method of centrifuging samples having different centrifugation parameters in the centrifuge of FIG. 1.

FIG. 2 illustrates a flowchart of one embodiment of a method 200 of centrifuging samples having different centrifugation parameters in the same centrifuge. In block 201, the sample input station 107 receives a number of samples 104-106. In block 202, the parameter assignment module 112 assigns each sample 104-106 at least one centrifugation parameter 101-103. As described above, the at least one centrifugation parameter 101-103 may be a centrifugal force, a centrifugation time (i.e. duration), a temperature of the centrifuge 108, or the like. In block 203, the samples 104-106 are transported from the sample input station 107 to the centrifuge 108. In block 204, the controller 111 compares the different centrifugation parameters 101-103 of the samples 104-106 received in block 201 and determines the centrifugation parameter of highest centrifugation intensity and the corresponding centrifugation protocol of highest centrifugation intensity. In block 205, the samples 104-106 are loaded into the centrifuge 108. In other embodiments, block 205 may be performed before block 204. In block 206, the loaded samples 104-106 are centrifuged according to the centrifugation protocol of highest centrifugation intensity. In some embodiments, block 206 may be performed after a specific period of time has elapsed, at a particular time of day, after all centrifuge buckets are occupied, or in response to receiving an explicit centrifugation command.

Figure 3A:
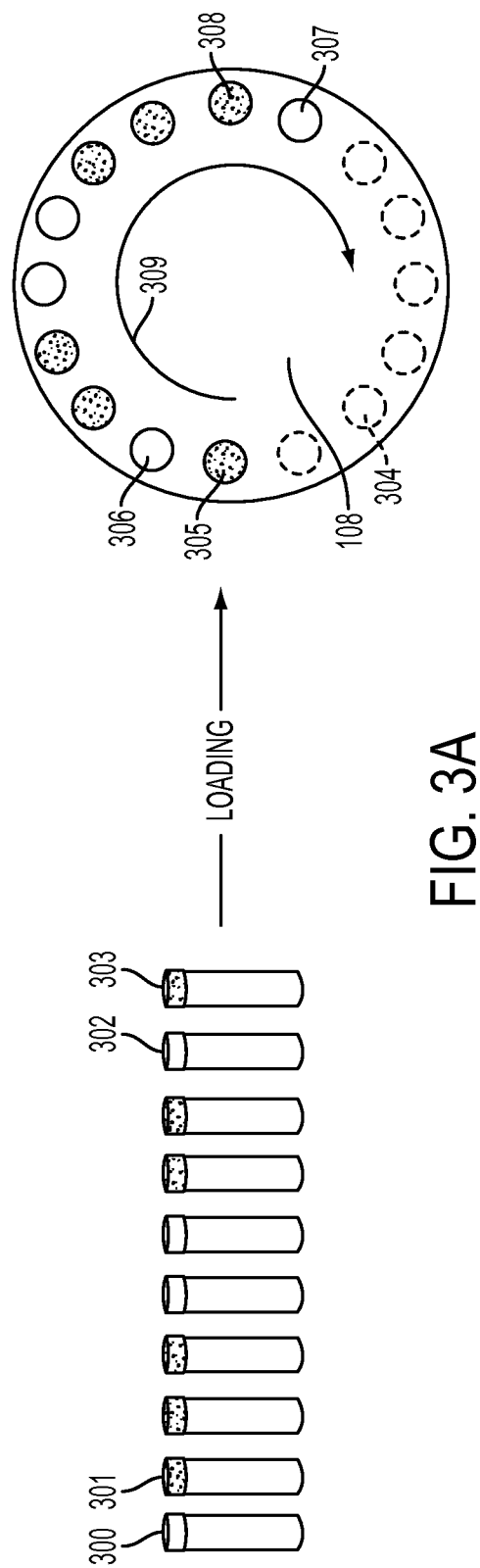
FIG. 3A illustrates the loading of samples having different centrifugation parameters into the centrifuge of FIG. 1 in the same order received by the automated sample workcell.

The loading of samples having different centrifugation parameters into the same centrifuge in the order they were received is depicted in FIG. 3A. A series of biological samples 300-303 are depicted on the left side of FIG. 3A in the order those samples 300-303 were loaded into the sample input station 107. The first sample loaded into sample input station was sample 303, followed by sample 302. The last sample to loaded into the sample input station 107 (as shown in FIG. 3A) was sample 300. Samples with shaded caps 301, 303 represent samples having assigned centrifugation parameters of higher centrifugation intensity (e.g., coagulation samples). Samples with un-shaded caps 300, 302 represent samples having assigned centrifugation parameters of lower centrifugation intensity (e.g., serum samples). The centrifuge 108 is depicted on the right side of FIG. 3A from a bird's eye view. The phantom circles represent unoccupied centrifuge buckets 304. The sample 303, which was first loaded into the sample input station 107, is first loaded into the centrifuge 108 in bucket 305. The next sample 302 is loaded into bucket 306. The last sample 300 received by the sample input station 107 is loaded into sample bucket 307, while the next-to-last sample 301 is loaded into bucket 308. In this illustrative embodiment, the loading of samples 300-303 into the centrifuge 108 is executed a clockwise order, indicated by arrow 309. As shown in FIG. 3A, centrifuge buckets 305, 308 that are loaded with coagulation samples 301, 303 are indicated as shaded circles, while centrifuge buckets 306, 307 that are loaded with serum samples 300, 302 are indicated as un-shaded circles with a solid border.

Figure 3B:
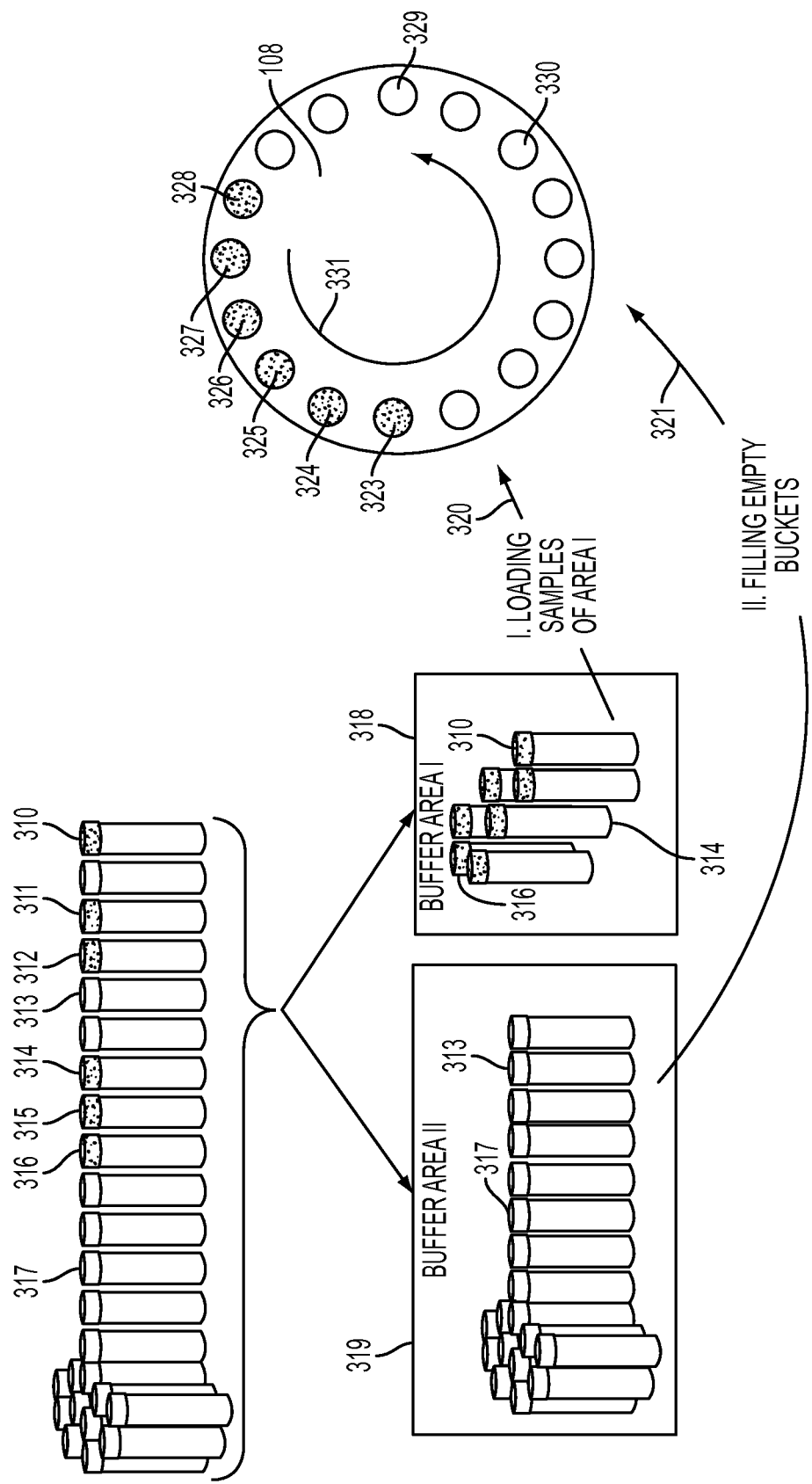
FIG. 3B illustrates the group-wise loading of samples having different centrifugation parameters into the centrifuge of FIG. 1.

The group-wise loading of samples having different centrifugation parameters into the same centrifuge is depicted in FIG. 3B. Similar to the embodiment of FIG. 3A, the samples 310-317 may be received by sample input station 107 in any order. The samples 310-317 may be received sequentially or may be received in the form of one or more sample racks (not shown). In FIG. 3B, six coagulation samples are shown as samples with shaded caps 310-312, 314-316, while nineteen serum samples are shown as samples with un-shaded caps 313, 317. In the illustrative embodiment, coagulation samples 310-312, 314-316 have been assigned a centrifugation parameter of higher centrifugation intensity. As shown in FIG. 3B, samples having a centrifugation parameter of higher centrifugation intensity are collected in a first buffer area 318. Other samples (e.g., serum samples 313, 317) are collected in a second buffer area 319. After a specific period of time has elapsed, at a particular time of day, after a certain number of samples are collected in the first buffer area 318 and/or the second buffer area 319, or in response to receiving an explicit centrifugation command, all samples that have been collected in the first buffer area 318 are loaded into centrifuge 108 (represented by arrow 320). The six centrifuge buckets 323-328 occupied by the six coagulation samples 310-312, 314-316 are depicted as shaded circles on the right side of FIG. 3B. Next, any empty buckets of centrifuge 108 are filled with samples that have been collected in the second buffer area 319 (represented by arrow 321). For instance, centrifuge buckets 329, 330 occupied by serum samples 313, 317 are depicted as un-shaded circles with solid borders on the right side of FIG. 3B. In this illustrative embodiment, the centrifuge 108 is filled to capacity by six coagulation samples and then ten serum samples in a counter-clockwise order, indicated by arrow 331. The remaining nine serum samples may be transferred to a second centrifuge 110 or may remain in the second buffer area 319 until the next run of the centrifuge 108.

Figure 4:
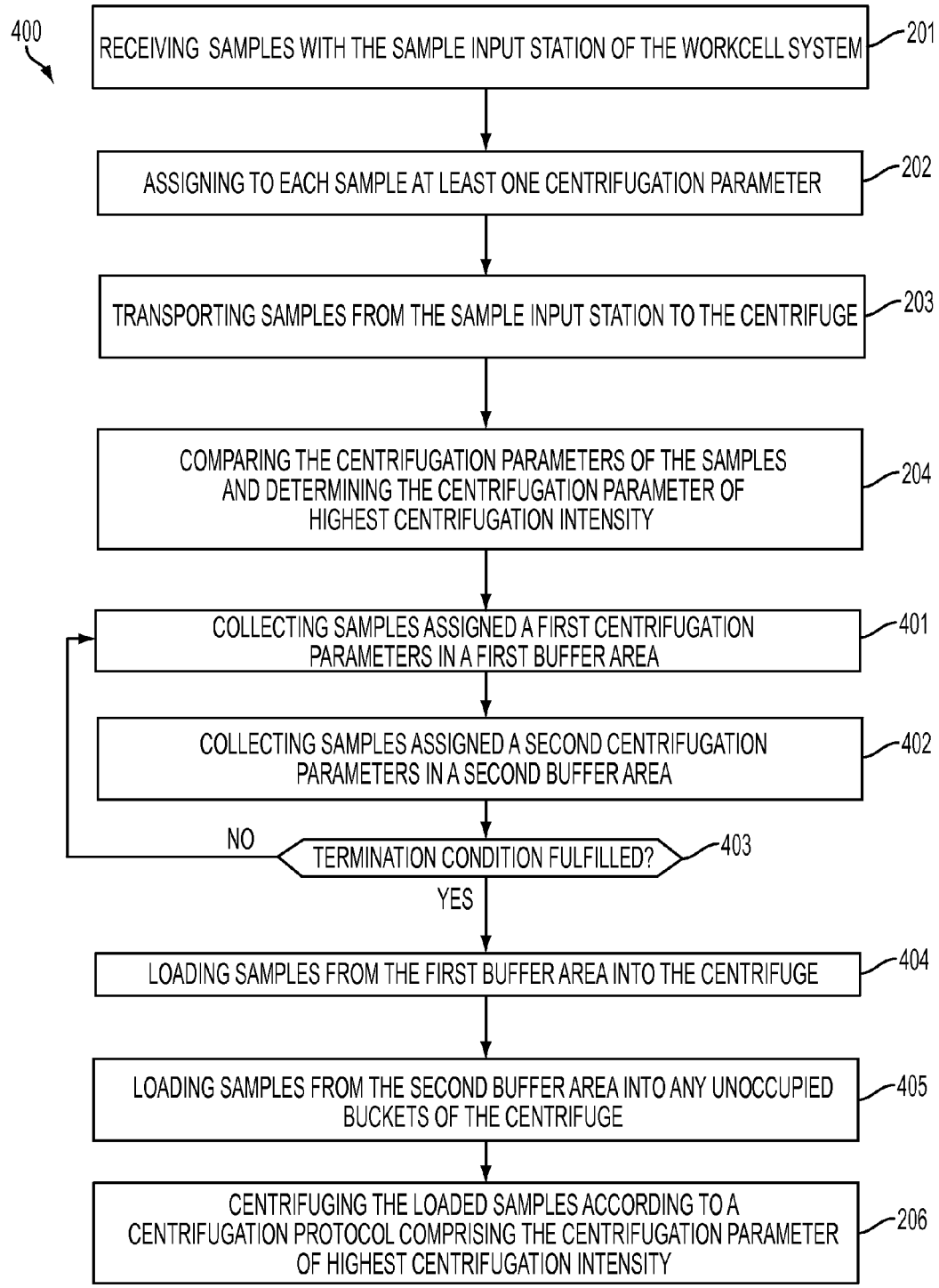
FIG. 4 illustrates a flowchart of another embodiment of a method of centrifuging samples having different centrifugation parameters in the centrifuge of FIG. 1, in which samples are collected in a plurality of buffer areas.

FIG. 4 illustrates a flowchart of another embodiment of a method 400 of centrifuging samples having different centrifugation parameters in the same centrifuge, in which the samples are collected in a number of buffer areas (as shown in FIG. 3B). The method 400 begins with blocks 201-204, which are performed as described with regard to FIG. 2. In block 401, samples 310-312, 314-316 having a particular centrifugation parameter (e.g., a centrifugation parameter of highest centrifugation intensity) are collected in the first buffer area 318. In block 402, samples 313, 317 having other centrifugation parameters are collected in the second buffer area 319. In block 403, the controller 111 checks whether a termination condition is fulfilled (e.g., whether a specific period of time has elapsed, a particular time of day has occurred, whether a certain number of samples are collected in the first buffer area 318 and/or the second buffer area 319, or whether an explicit centrifugation command has been received). If the condition is fulfilled, the method 400 proceeds to block 404 in which as many samples 310-312, 314-316 from the first buffer area 318 as possible are loaded into the centrifuge 108. In block 405, any unoccupied buckets of centrifuge 108 are filled by loading samples 313, 317 from the second buffer area 319 into the centrifuge 108. In block 206, the loaded samples 310-317 are centrifuged according to centrifugation protocol of highest centrifugation intensity (as determined in block 204).

Figure 5:
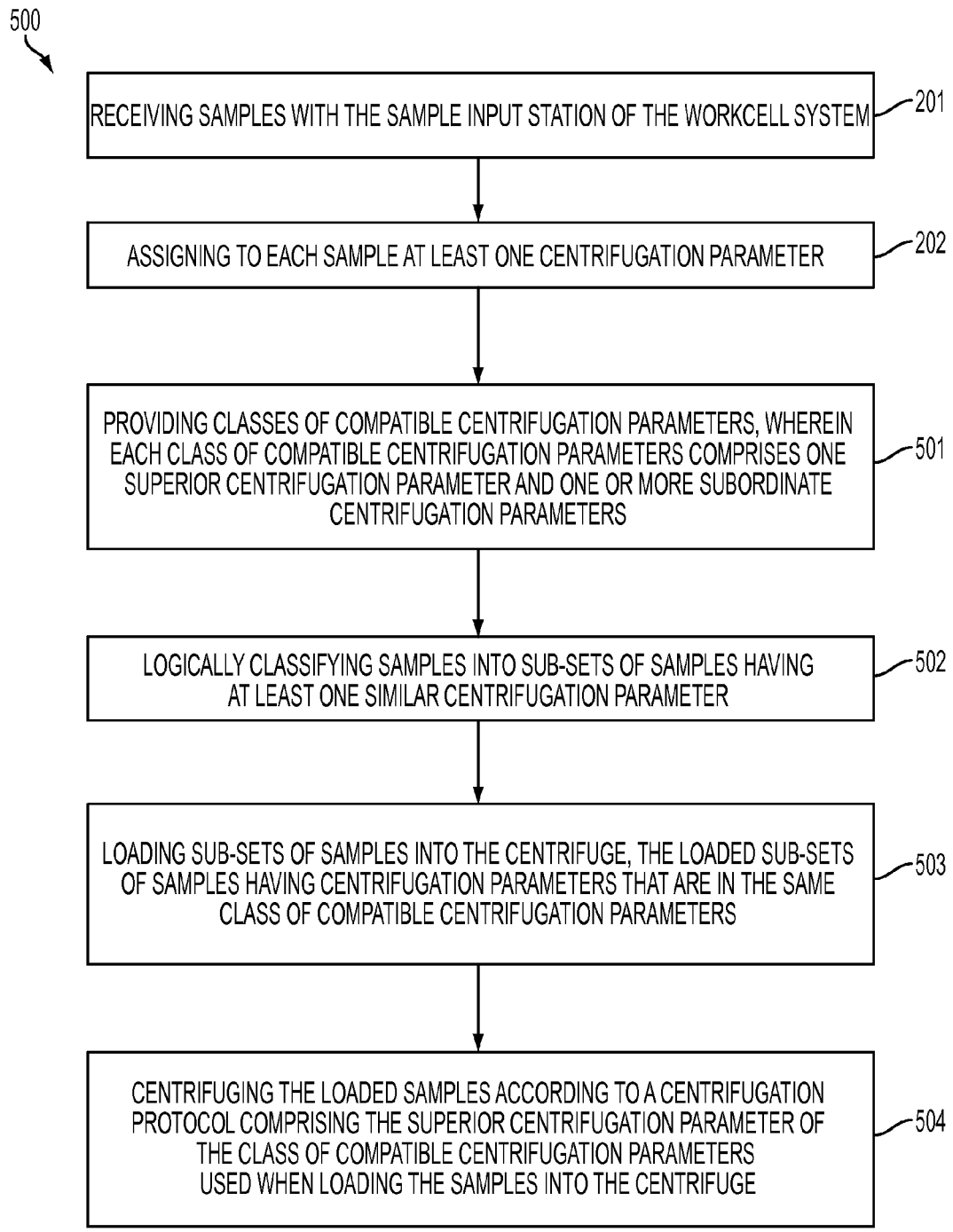
FIG. 5 illustrates a flowchart of another embodiment of a method of centrifuging samples having different centrifugation parameters in the centrifuge of FIG. 1, according to classes of compatible centrifugation parameters.

FIG. 5 illustrates a flowchart of another embodiment of a method 500 of centrifuging samples having different centrifugation parameters in the same centrifuge, according to classes of compatible centrifugation parameters. The method 500 begins with blocks 201, 202, which are performed as described with regard to FIG. 2. In block 501, the workcell system 100 provides classes of compatible centrifugation parameters, wherein each class of compatible centrifugation parameters comprises one superior centrifugation parameter and at least one subordinate centrifugation parameter. The classes of compatible centrifugation parameters can be provided, for example, by a relational database, by a configuration file, or by hard-coding into an application software module. In block 502, the samples received by the workcell system 100 in block 201 are logically classified into sample sub-sets according to their assigned centrifugation parameter(s). All samples assigned to the same sample sub-set share at least one centrifugation parameter. In block 503, samples selected from a class of compatible sample sub-sets are loaded into the centrifuge 108 (e.g., one of the classes shown in Table 4). In block 504, the samples loaded into the centrifuge 108 in block 503 are centrifuged according to the superior centrifugation parameter of the class. If samples from only one sample sub-set are loaded in block 503, the common centrifugation parameter of that sample sub-set is used as the superior centrifugation parameter.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the apparatus, systems, and methods described herein. It will be noted that alternative embodiments of the apparatus, systems, and methods of the present disclosure may not include all of the features described yet still benefit from at least some of the advantages of such features. Those of ordinary skill in the art may readily devise their own implementations of the apparatus, systems, and methods that incorporate one or more of the features of the present invention and fall within the spirit and scope of the present disclosure as defined by the appended claims.

The invention claimed is:

1. A method comprising:
receiving a first plurality of samples, each of the first plurality of samples being linked to a requested analysis selected from among a plurality of analysis types;
assigning a first centrifugation parameter or a second centrifugation parameter to each of the first plurality of samples in response to the requested analysis linked to that sample, the second centrifugation parameter being different from the first centrifugation parameter;
loading a second plurality of samples into a centrifuge, the second plurality of samples being selected from among the first plurality of samples and comprising samples that have been assigned the first centrifugation parameter and samples that have been assigned the second centrifugation parameter;
determining a centrifugation parameter of highest centrifugation intensity from among the first and second centrifugation parameters assigned to samples in the second plurality of samples; and
centrifuging the second plurality of samples according to a centrifugation protocol comprising the centrifugation parameter of highest centrifugation intensity.

2. The method of claim 1, wherein assigning a first centrifugation parameter or a second centrifugation parameter to each of the first plurality of samples comprises assigning at least one centrifugation parameter of higher centrifugation intensity to each sample linked to a requested coagulation analysis and assigning at least one centrifugation parameter of lower centrifugation intensity to each sample linked to a requested clinical chemistry analysis.

3. The method of claim 2, wherein loading the second plurality of samples into the centrifuge comprises loading at least one sample linked to a requested coagulation analysis into the centrifuge and loading at least one sample linked to a requested clinical chemistry analysis into the centrifuge.

4. The method of claim 1, further comprising:
collecting samples from the first plurality of samples that are assigned the first centrifugation parameter in a first buffer area;
collecting samples from the first plurality of samples that are assigned the second centrifugation parameter in a second buffer area; and
determining whether a termination condition is fulfilled prior to loading the second plurality of samples into the centrifuge.

5. The method of claim 4, wherein loading the second plurality of samples into the centrifuge comprises:
loading samples collected in the first buffer area into the centrifuge; and
loading samples collected in the second buffer area into the centrifuge to fill one or more unoccupied centrifuge buckets remaining after loading the samples collected in the first buffer area.

6. The method of claim 4, wherein collecting samples in the second buffer area comprises collecting samples that are received with greater frequency than samples collected in the first buffer area.

7. The method of claim 4, wherein the second centrifugation parameter is of lower centrifugation intensity than the first centrifugation parameter.

8. The method of claim 4, wherein determining whether the termination condition is fulfilled comprises one of determining whether a predefined period of time has elapsed, determining whether a particular time of day has occurred, determining whether a predefined number of samples have been collected in the first buffer area, determining whether a predefined number of samples have been collected in both the first and second buffer areas, and determining whether an explicit centrifugation command has been received.

9. The method of claim 1, further comprising logically classifying the first plurality of samples into a plurality of classes of compatible centrifugation parameters, each of the plurality of classes of compatible centrifugation parameters including a superior centrifugation parameter and one or more subordinate centrifugation parameters, wherein the second plurality of samples are selected from among one of the plurality of classes of compatible centrifugation parameters.

10. The method of claim 1, wherein assigning a first centrifugation parameter or a second centrifugation parameter to each of the first plurality of samples comprises:
   reading an indicator on each of the first plurality of samples to obtain information regarding the requested analysis linked to that sample; and
   processing the obtained information using a rules engine.

* * * * *